(12) United States Patent
Talley et al.

(10) Patent No.: US 6,441,014 B2
(45) Date of Patent: Aug. 27, 2002

(54) CRYSTALLINE FORM OF 4-[5-METHYL-3-PHENYLISOXAZOL-4-YL]BENZENESULFONAMIDE

(75) Inventors: John J Talley, Brentwood, MO (US); John R Medich, Curnee, IL (US); Kathleen T McLaughlin, Arlington Heights, IL (US); Henry T Gaud, Evanston, IL (US); Edward E Yonan, Carol Stream, IL (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 09/741,213

(22) Filed: Dec. 19, 2000

Related U.S. Application Data

(63) Continuation of application No. 09/246,276, filed on Feb. 8, 1999, now abandoned, which is a continuation of application No. 08/909,512, filed on Aug. 12, 1997, now abandoned.
(60) Provisional application No. 60/024,378, filed on Aug. 14, 1996.

(51) Int. Cl.$^7$ .................. A61K 31/42; C07D 261/08
(52) U.S. Cl. ........................... 514/378; 548/247
(58) Field of Search ................... 514/378; 548/247

(56) References Cited

U.S. PATENT DOCUMENTS

| 5,633,272 A | 5/1997 | Talley et al. ............. 514/378 |
| 5,643,933 A | 7/1997 | Talley et al. ............. 514/372 |

FOREIGN PATENT DOCUMENTS

| WO | 95/00501 | 1/1995 |
| WO | 96/38442 | 5/1996 |

*Primary Examiner*—Flona T. Powers
(74) *Attorney, Agent, or Firm*—McDonnell Boehnen Hulbert & Berghoff

(57) ABSTRACT

A stable crystalline form of 4-[5-methyl-3-phenylisoxazol-4-yl]benzenesulfonamide is described. This crystal structure, designated Form B, is more stable, has favorable handling properties and is characterized by its melting point, x-ray and other physical characterizations.

13 Claims, 5 Drawing Sheets

CRYSTALLINE FORM OF 4-[5-METHYL-3-PHENYLISOXAZOL-4-YL]BENZENESULFONAMIDE

This is a continuation of U.S. application Ser. No. 09/246,276 filed Feb. 8, 1999, now abandoned, which is a continuation of application Ser. No. 08,909,512, filed Aug. 12, 1997, now abandoned, which claims priority of application Ser. No. 60/024,378, filed Aug. 14, 1998.

FIELD OF THE INVENTION

This invention is in the field of antiinflammatory pharmaceutical agents and specifically relates to a crystalline form of 4-[5-methyl-3-phenylisoxazol-4-yl]benzenesulfonamide, methods of preparing the crystalline form, pharmaceutical compositions and methods for treating cyclooxygenase-2 (COX-2) associated disorders, including inflammation.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects related to inhibition of cyclooxygenase-1 (COX-1).

A group of substituted isoxazoles are described in U.S. Pat. No. 5,633,272, to Talley et al., and International Application WO96/25405. The compounds are described to be useful for the treatment of inflammation and inflammation-associated disorders. 4-[5-Methyl-3-phenylisoxazol-4-yl]benzenesulfonamide shows potential as a selective inhibitor of COX-2 over COX-1.

With all pharmaceutical compounds and compositions, the chemical and physical stability of a drug compound is important in the commercial development of that drug substance. Such stability includes the stability at ambient conditions, especially to moisture and under storage conditions. Elevated stability at different conditions of storage is needed to anticipate the different possible storage conditions during the lifetime of a commercial product. A stable drug avoids the use of special storage conditions as well as frequent inventory replacement. A drug compound must also be stable during the manufacturing process which often requires milling of the drug to achieve drug material with uniform particle size and surface area. Unstable materials often undergo polymorphic changes. Therefore, any modification of a drug substance which enhances its stability profile provides a meaningful benefit over less stable substances.

It has now been discovered that 4-[5-methyl-3-phenylisoxazol-4-yl]benzenesulfonamide can be prepared in different crystal forms. An earlier material (Form "A") is unstable after mechanical grinding (milling) and is also thermally unstable. A recently determined crystalline form (Form "B") is described which is more stable and has improved physical properties.

DETAILED DESCRIPTION OF THE INVENTION

It has been discovered that 4-[5-methyl-3-phenylisoxazol-4-yl]benzenesulfonamide can be prepared in a crystalline form designated "Form B". Form B can be characterized by the following methods.

Melting

Melting points were performed either on a Thomas Hoover melting point apparatus or a Mettler FP900 Thermosystem melting point apparatus. Melting ranges were determined by differential scanning calorimetry on a TA Instruments Differential Scanning Calorimeter (Model 2100 controller, Model 912 dual calorimeter). The sample (1–2 mg) was placed in an unsealed aluminum pan and heated at 10° C./minute.

Figure 1:
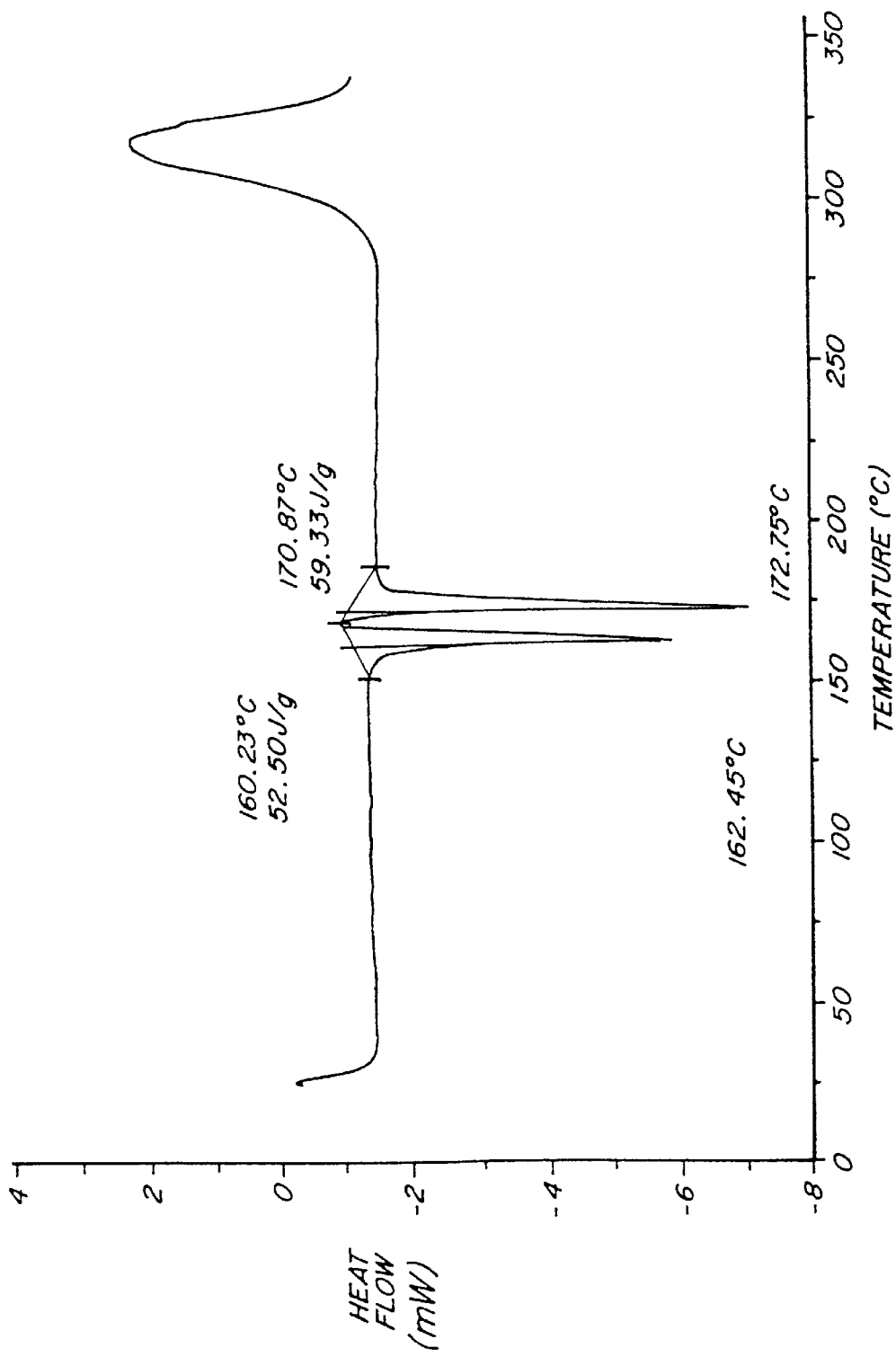
FIG. 1 shows a differential scanning calorimetry (DSC) profile of 4-[5-methyl-3-phenylisoxazol-4-yl]benzenesulfonamide Form A.
Figure 2:
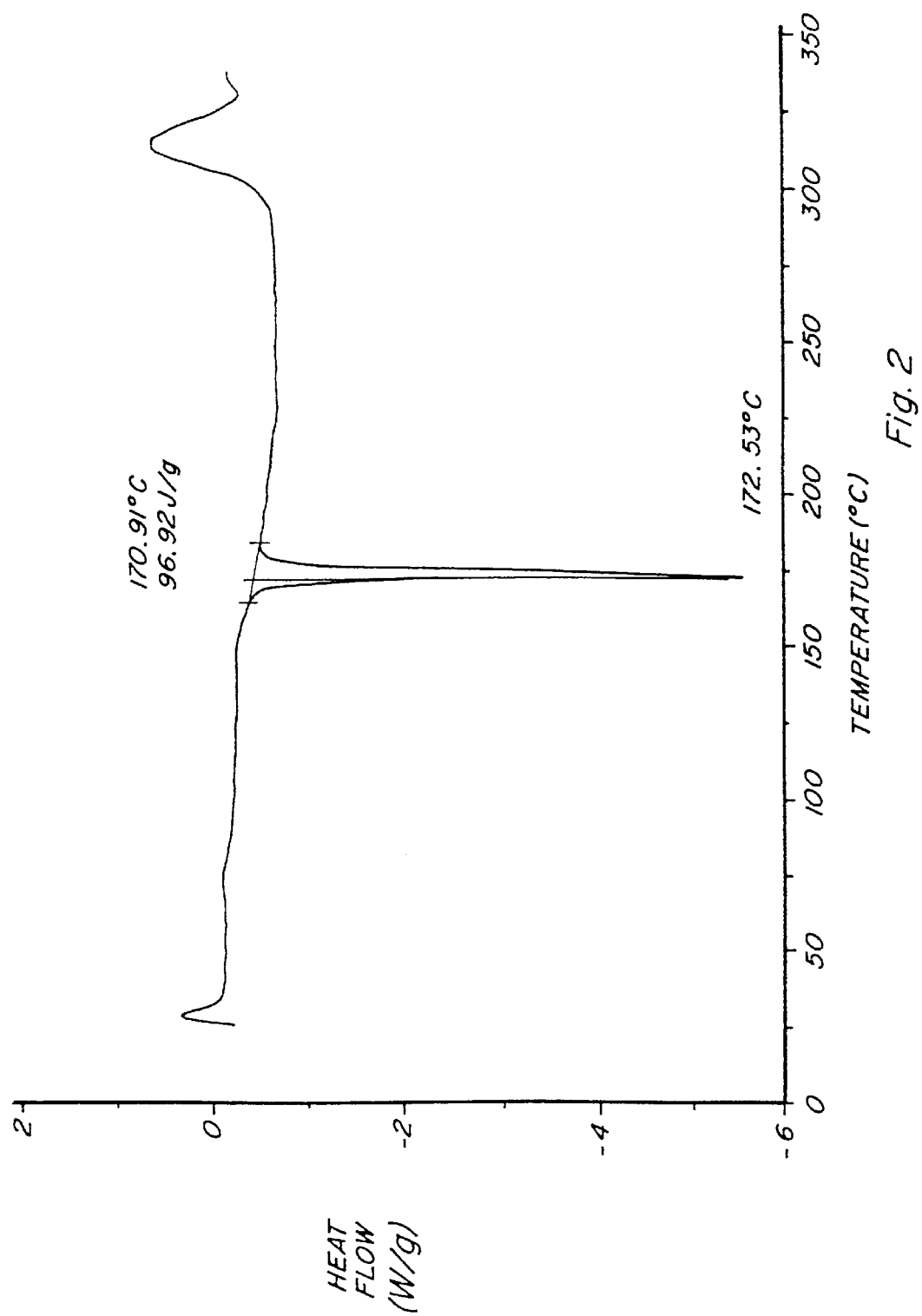
FIG. 2 shows a differential scanning calorimetry (DSC) profile of 4-[5-methyl-3-phenylisoxazol-4-yl]benzenesulfonamide Form B.

Form A showed an onset of melting at 160.2° C. with an imbedded exotherm at 170.9° C. due to crystal rearrangement (see FIG. 1). Form B showed an onset of melting at 170.9° C. (peak 172.5° C.). An example of the DSC of Form B is shown in FIG. 2.

Infrared Spectroscopy

Figure 3A:
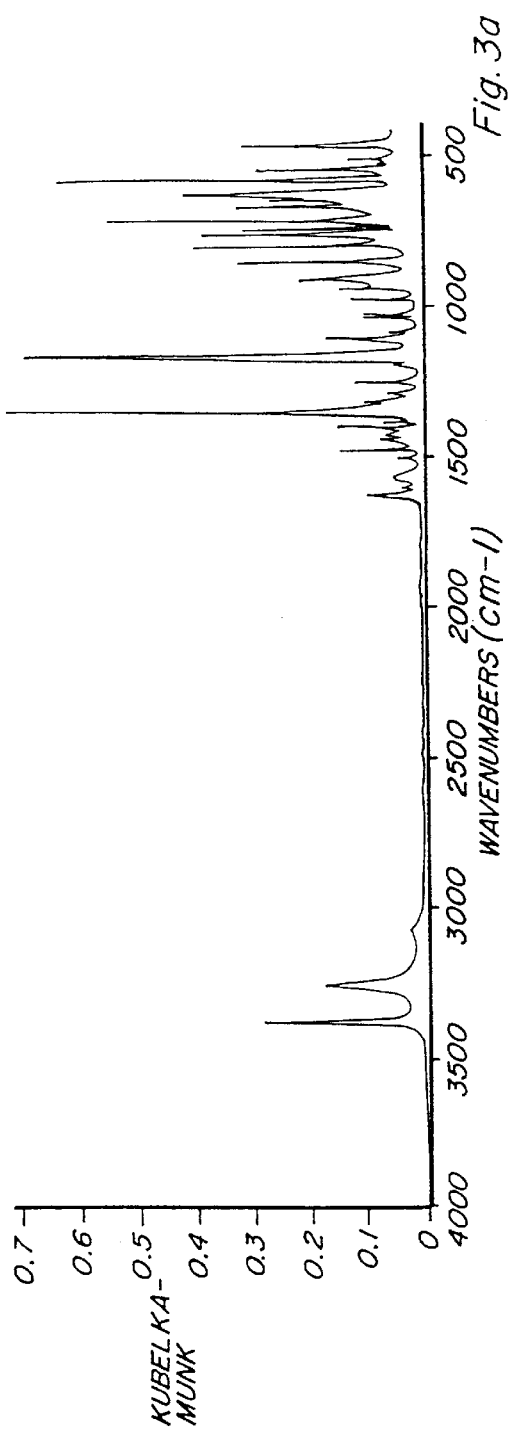
FIG. 3a shows an infrared spectrum of 4-[5-methyl-3-phenylisoxazol-4-yl]benzenesulfonamide Form B.
Figure 3B:
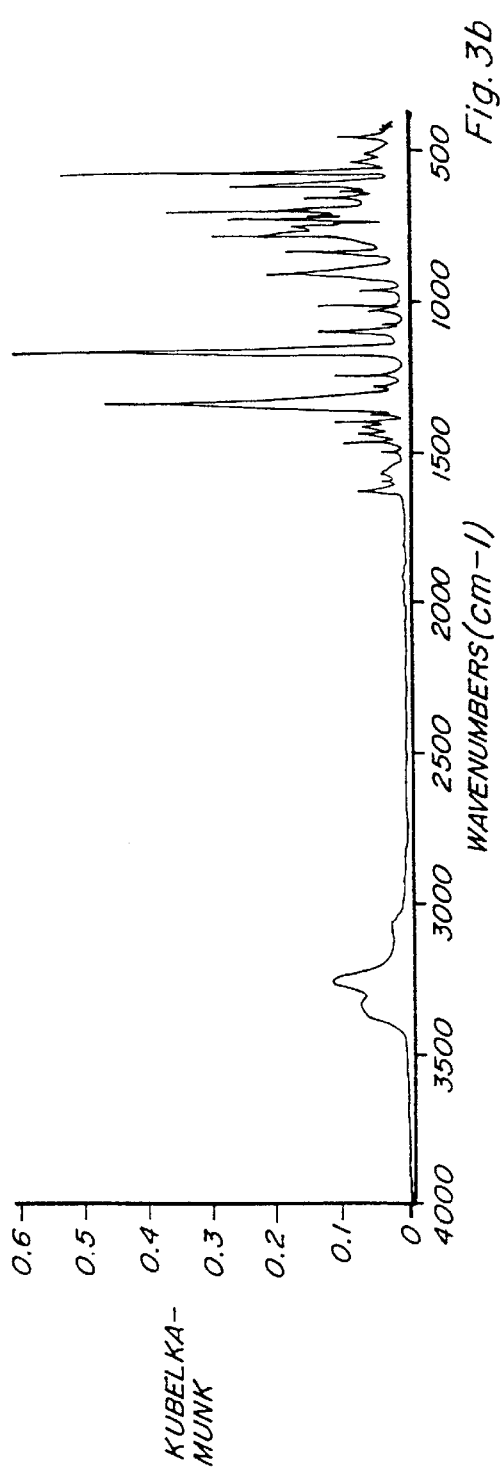
FIG. 3b shows an infrared spectrum of 4-[5-methyl-3-phenylisoxazol-4-yl]benzenesulfonamide Form A.

Infrared spectra were obtained with a Nicolet DRIFT (diffused reflectance infrared fourier transform) Magna System 550 spectrophotometer. A Spectra-Tech Collector system and a 3 mm sample cup were used. Samples (2%) were analyzed in KBr and scanned from 400 to 4000 cm$^{-1}$. An example of an infrared absorption spectra of Form B is shown in FIG. 3a, and that of Form A is shown in FIG. 3b. The Y-axis represents corrected reflectance in Kubella-Munk units.

The infrared spectrum of Form B is characterized by absorptions at about 3377, 1170, 1151, 925, 844, 745, 729, and 534 cm$^{-1}$ which are different than that observed in the Form A spectra. The infrared spectrum of Form A is characterized in part by an absorption at about 723 cm$^{-1}$ which is different than that observed in the Form B spectra. Form B crystals of the present invention preferably display an infrared spectrum substantially the same as that shown in FIG. 3a.

X-ray Powder Diffraction

The analysis was performed with a Siemens D5000 powder diffractometer. Raw data was measured for 2θ values from 2 to 50, with steps of 0.020 and step periods of 2 seconds.

Figure 4:
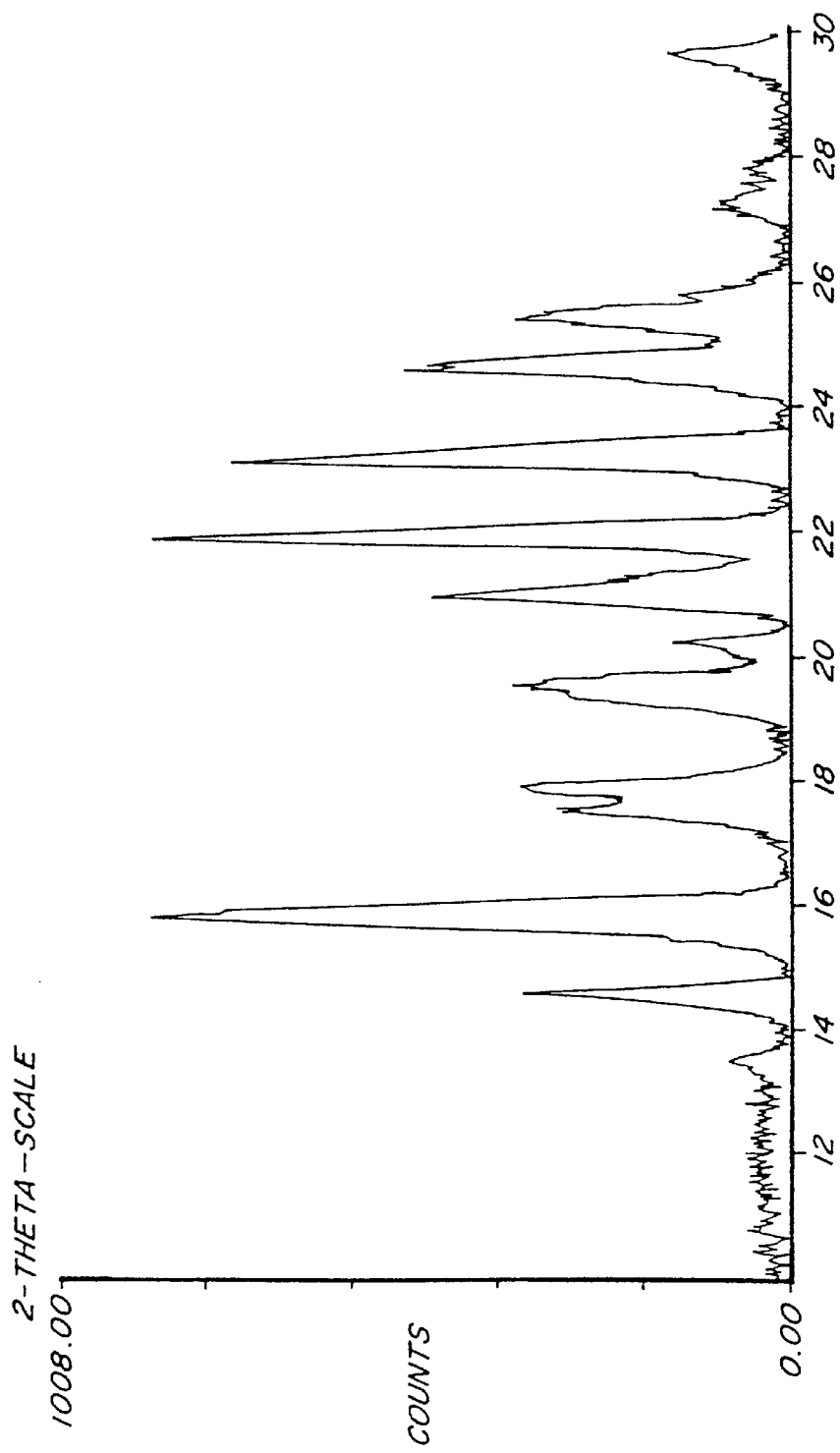
FIG. 4 shows an X-ray diffraction pattern of 4-[5-methyl-3-phenylisoxazol-4-yl]benzenesulfonamide Form A.
Figure 5:
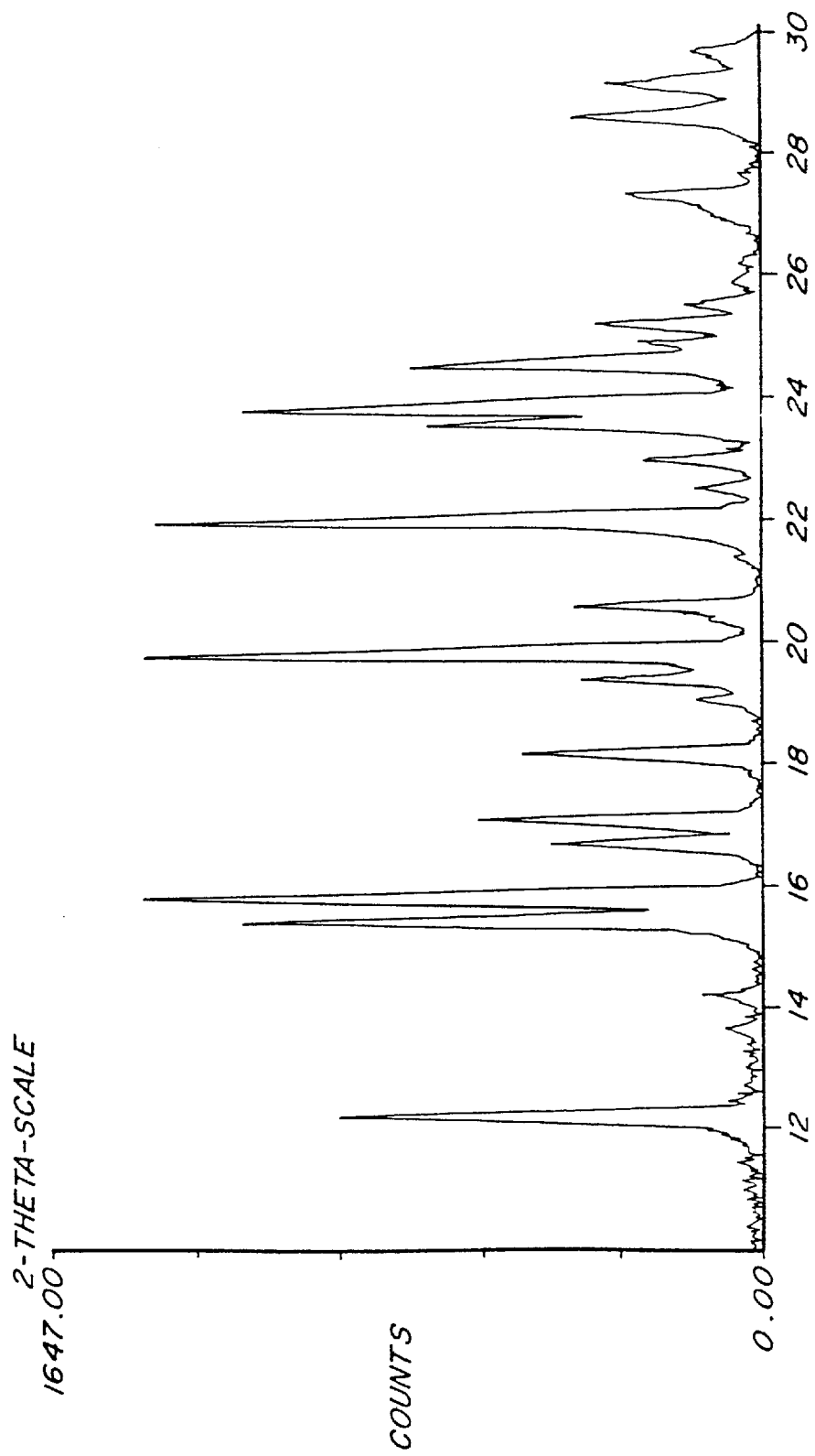
FIG. 5 shows an X-ray diffraction pattern of 4-[5-methyl-3-phenylisoxazol-4-yl]benzenesulfonamide Form B.

Table I sets out the significant parameters of the main peaks in terms of 2θ values and intensities for Form B. An example of the x-ray diffraction pattern for Form A is shown in FIG. 4. An example of the x-ray diffraction pattern for Form B is shown in FIG. 5. Significant differences between Form A and Form B are evident at 12.221, 15.447, 17.081, 19.798 and 23.861.

TABLE I

| Peak No. | Angle-2θ (deg) | D spacing | Peak Cps | I/Imax (%) |
| --- | --- | --- | --- | --- |
| 1 | 12.221 | 7.2361 | 502.38 | 63.29 |
| 2 | 13.693 | 6.4617 | 38.03 | 4.79 |
| 3 | 14.227 | 6.2203 | 51.46 | 6.48 |
| 4 | 15.447 | 5.7314 | 599.94 | 75.58 |
| 5 | 15.801 | 5.6039 | 793.79 | 100.00 |
| 6 | 16.678 | 5.3110 | 239.95 | 30.23 |
| 7 | 17.081 | 5.1868 | 331.31 | 41.74 |
| 8 | 18.165 | 4.8796 | 270.21 | 34.04 |
| 9 | 19.066 | 4.6510 | 73.16 | 9.22 |
| 10 | 19.400 | 4.5717 | 200.13 | 25.21 |
| 11 | 19.798 | 4.4807 | 789.23 | 99.43 |
| 12 | 20.578 | 4.3126 | 209.43 | 26.38 |
| 13 | 22.008 | 4.0354 | 691.33 | 87.09 |
| 14 | 22.540 | 3.9414 | 71.87 | 9.05 |
| 15 | 22.975 | 3.8678 | 137.23 | 17.29 |
| 16 | 23.580 | 3.7699 | 394.27 | 49.67 |
| 17 | 23.861 | 3.7261 | 602.27 | 75.87 |
| 18 | 24.553 | 3.6226 | 397.23 | 50.04 |
| 19 | 25.206 | 3.5302 | 192.44 | 24.24 |
| 20 | 25.560 | 3.4822 | 77.74 | 9.79 |
| 21 | 25.940 | 3.4320 | 31.47 | 3.96 |
| 22 | 26.200 | 3.3985 | 20.87 | 2.63 |
| 23 | 27.295 | 3.2646 | 151.54 | 19.09 |
| 24 | 28.595 | 3.1191 | 207.74 | 26.17 |
| 25 | 29.124 | 3.0636 | 161.44 | 20.34 |
| 26 | 29.656 | 3.0099 | 73.94 | 9.32 |

Form B can be prepared by the recrystallization of 4-[5-methyl-3-phenylisoxazol-4-yl]benzenesulfonamide from a suitable solvent. To prepare Form B, 4-[5-methyl-3-phenylisoxazol-4-yl]benzenesulfonamide is dissolved in a volume of solvent and cooled until crystals form. Preferably, the compound is added to a solvent at a temperature of at least about 25° C. More preferably, the temperature of the solvent is between 30° C. and the boiling point of the solvent. An even more preferred temperature is in a range of about 65–75° C.

Alternatively, hot solvent may be added to the compound and the mixture can be cooled until crystals form. Preferably, the solvent is at a temperature of at least 25° C. More preferably, the temperature of the solvent is at a temperature in the range of about 50–80° C. Even more preferred, the temperature is in a range of about 65–75° C.

Preferably, the compound is mixed with an amount of solvent over about 3 times the weight of the compound. More preferred, the solvent to compound ratio is about 7 to about 10 times.

Preferably the solution is cooled slowly to precipitate Form B. More preferably, the solution is cooled at a rate slower than about 0.5° C./minute. Even more preferably, the solution is cooled at a rate of about 0.3° C./minute or slower.

A suitable solvent is a solvent or mixture of solvents which dissolves the compound and any impurities at an elevated temperature, but upon cooling, preferentially precipitates Form B. A suitable solvent is selected from an alcohol, methyl tert-butyl ether, methyl ethyl ketone and a combination of solvents selected from alcohol, methyl tert-butyl ether, acetonitrile, water, acetone, tetrahydrofuran and methyl ethyl ketone. An alcohol or aqueous alcohol is preferred. A more preferred solvent is selected from methanol, aqueous methanol, ethanol, aqueous ethanol, isopropyl alcohol and aqueous isopropyl alcohol. Even more preferred is aqueous methanol, methanol, ethanol 3A, aqueous ethanol and a mixture of isopropanol/methanol.

Alternatively, the compound is dissolved in one solvent and a co-solvent is added to aid in the crystallization of the desired form.

The crystals of Form B so formed are separated from the solvent such as by filtration or centrifugation. Preferably, the crystals are dried, and more preferably at a temperature in the range of about 30° C. to about 100° C. Even more preferably, the crystals are dried under vacuum.

Alternatively, Form B can be prepared by heating Form A at a temperature sufficient to convert to Form B. Preferably, Form A is heated at a temperature in the range of 50° C. to about 140° C.

Preparation

The following examples contain detailed descriptions of the methods of preparation of Form B. These detailed descriptions fall within the scope, and serve to exemplify the invention. These detailed descriptions are presented for illustrative purposes only and are not intended as a restriction on the scope of the invention. All parts are by weight and temperatures are in degrees Centigrade unless otherwise indicated.

4-[5-Methyl-3-phenylisoxazol-4-yl]benzenesulfonamide was prepared by the following method where ethanol 3A is an aqueous ethanol (5% water) denatured with methanol:

EXAMPLE 1

Step 1. Preparation of Deoxybenzoin Oxime

Sodium acetate trihydrate (152.5 g, 1.12 mole, 1.1 eq.) was added to deoxybenzoin (200 g, 1.02 mole) and dissolved with ethanol (3A, 0.8 L) and water (0.24 L) in a 5 L flask with mechanical stirrer, reflux condenser, and thermometer. The solution was stirred and heated to 70±1° C. Water (0.1 L) was added to hydroxylamine hydrochloride (78.0 g, 1.12 mole, 1.1 eq.) in a separate 500 ML flask with stirring. The hydroxylamine hydrochloride solution was transferred to the deoxybenzoin solution, while the reaction mixture was kept at about 70° C. The mixture was heated to boiling (about 84° C.) and held at this temperature for 40 minutes. The mixture was cooled to 40° C. in two hours and charged water (10.5 L) into the reaction mixture. The reaction mixture was cooled to 20° C. over another hour with stirring. Crystals of pure oxime formed which were isolated by filtration (Buchner funnel, No. 1 Whatman filter paper) using house vacuum, washed with a mixture of 50 mL of 3A ethanol and 100 mL of water, and with water (1 L). The solid was dried with vacuum for 2 hours, and at 55° C. under house vacuum for 12 hours to yield pure deoxybenzoin oxime (213.2 g, 99%).

Step 2. Preparation of 5-hydroxy-5-methyl-3,4-diphenylisoxazoline

The deoxybenzoin oxime (Step 1) was dissolved in anhydrous THF (565 mL) under a nitrogen atmosphere. The solution was cooled to −20° C. The solution was treated with lithium diisopropylamide (2 M, 800 mL, 1.60 mol) while allowing the reaction temperature to warm to 10–15° C. The reaction mixture to was cooled to −10° C. to −20° C. and anhydrous ethyl acetate (218 mL) was added to the solution while allowing the reaction temperature to rise to a maximum of 25° C. and held for 30 minutes at 25° C. The reaction mixture was cooled to about 0° C. Water was added to a quench flask and cooled to 0–5° C. The pre-cooled reaction mixture was transferred from the reaction flask to the quench flask while maintaining the temperature of the quench mixture below 25° C. The quenched mixture was cooled to 0–5° C. Hydrochloric acid (12 M). was added to the mixture, keeping the temperature below 25° C. during the addition by controlling the addition rate and stirred until all the solids dissolve (~5 minutes). The pH of the stirred mixture was measured to be pH 3–4. The layers were separated and the organic layer was removed. Heptane was added to the organic layer with stirring. The organic layer was distilled until the pot temperature reached 90–91° C. The solution was cooled to 5° C. and filtered. The solid was washed with two 300 mL portions of ethyl acetate-heptane (20/80), cooled to 5° C. The solid product was dried on the funnel for several hours then dried at ambient under vacuum with a nitrogen sweep over the weekend to yield the isoxazoline (108.75 g, 57.7%).

Step 3. Preparation of 4-[(5-methyl-3-phenyl)-4-isoxazolyl]benzenesulfonamide

5-Hydroxy-5-methyl-3,4-diphenylisoxazoline (Step 2) (142 g, 0.56 mol) was dissolved in dichloromethane (568 mL) in a 3 L roundbottom flask equipped with a heating mantle, mechanical stirrer, cold water condenser, J-KEM temperature controller and thermocouple, forming a slurry. The slurry was stirred and cooled to <10° C. Chlorosulfonic acid (335 mL, 586.3 g, 5.04 mol) was added to the slurry, keeping the temperature of the flask below 20° C. by controlling the addition. The mixture was heated to reflux (ca. 40° C.), maintained for 5 hours, then cooled to 0–5° C. The cooled reaction solution was slowly transferred to a 3 L 3-necked roundbottom flask (mechanical stirrer and thermocouple) containing water (1000 ml) previously cooled to 0–5° C., using vigorous agitation and keeping the pot temperature below 10° C. The mixture was stirred for an additional 5 minutes. The layers were separated. In a separate 3 L flask (mechanical stirrer, external ice/salt bath, thermocouple) 28% ammonium hydroxide (700-mL) was cooled to 0–5° C. The methylene chloride solution was transferred to the stirred ammonium hydroxide solution, keeping the temperature below 10° C. The mixture was stirred at ambient temperature for 60 minutes. The resulting slurry was filtered and the solid was washed with water (200 ml) and dried, yielding the 4-[(5-methyl-3-phenyl)-4-isoxazolyl]benzenesulfonamide as a white solid (94.3 g, 53.5%).

Step 4. Recrystallization of 4-[(5-methyl-3-phenyl)-4-isoxazolyl]benzenesulfonamide The 4-[(5-methyl-3-phenyl)-4-isoxazolyl]benzenesulfonamide from Step 3 was dissolved in 300 mL of boiling methyl ethyl ketone (2-butanone) and diluted with 10% aqueous isopropyl alcohol (300 mL, (270 mL anhydrous isopropyl alcohol and 30 mL of water)). The material was cooled to room temperature, whereupon crystals formed. The crystals were isolated by filtration and dried in a vacuum drying oven (10 mm Hg, 100° C.) to afford pure Form B (112.95 g, 65%): mp 172–173° C.

EXAMPLE 2

"4-[5-Methyl-3-phenylisoxazol-4-yl]benzenesulfonamide (Example 1, step 3) (3 g) was combined with 80% ethanol 3A/20% water (9 ml) and heated until solids dissolved. The flask was cooled with a tap water bath and held for 1 hour to form a precipitate. The solid was filtered off and washed with ethanol 3A. The material was heated to dryness under vacuum (50–60° C., 20 in Hg). The material formed was identified as Form B."

EXAMPLE 3

"4-[5-Methyl-3-phenylisoxazol-4-yl]benzenesulfonamide (Example 1, step 3) (10 g) was combined with ethanol 3A (100 ml ) and heated until the solids dissolved (about 70° C.). The flask was cooled to 20–25° C. over 1.5 hours and held for 30 minutes to form a precipitate. The solid was filtered off (Whatman # 1 filter paper) and washed with water. The material was heated to dryness under vacuum (90° C., 50–100 mm Hg). The material formed was identified as Form B."

EXAMPLE 4

"4-[5-Methyl-3-phenylisoxazol-4-yl]benzenesulfonamide (Example 1, step 3) (9.8 g), methanol (73.5 mL) and water (24.5 mL) were combined and heated to 65–70° C. The solution was held for about 10 minutes and filtered while hot to remove any particulate matter. The solution was cooled slowly to 50° C. (about 0.3° C./min) held at 50° C. for 1 hour (crystallization begins during the hold period). The solution was further cooled to 5° C. (about 0.3° C./min) and held at 5° C. for 1 hour. The product was isolated by filtration and washed with 10 mL of cold methanol/water (75/25). The product was dried at 95–100° C. for 4 hours to give 8.55 g of Form B."

EXAMPLE 5

Methanol/isopropanol (80/20, 120 ml) was added to 4-[5-methyl-3-phenylisoxazol-4-yl]benzenesulfonamide (Example 1, step 3) (25 g) and heated to about 68° C. The solution was held for about 15 minutes and filtered with a glass filtering funnel, while hot, to remove any particulate matter. The solution was cooled slowly to 5° C. over 3.3 hours (about 0.3° C./min) and held at 5° C. for 2 hours. The product was isolated by filtration and washed with 10 mL of cold methanol/isopropanol (80/20). The product was dried at 95–100° C. for 3 hours to give 11 g of Form B.

Comparative Example 6

"4-[5-Methyl-3-phenylisoxazol-4-yl]benzenesulfonamide (Example 1, step 3)(10 g) was combined with 20 mL of water:methanol (25:75), and heated until the solids dissolved. The flask containing the solution was set in ice and the mixture cooled rapidly to <10° C. with no crystallization observed on cooling. A few crystals were observed forming on bottom of flask, and soon crystallization was rapid. Let stand for about 10 minutes. The solid was filtered off and washed with 75% aqueous methanol. The material was heated to dryness under vacuum w/nitrogen bleed (50–60° C., 20 in Hg). Material formed was identified as Form A."

The present invention also comprises a method of treating or preventing a cyclooxygenase-2 associated disorder such as inflammation in a subject, the method comprising treating the subject having or susceptible to such inflammation or disorder with a therapeutically-effective amount of crystalline Form B of 4-[5-methyl-3-phenylisoxazol-4-yl]benzenesulfonamide.

Form B of 4-[5-methyl-3-phenylisoxazol-4-yl]benzenesulfonamide would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, Form B would be useful to treat arthritis, including but not limited to rheumatoid arthritis, spondyloarthropathies, gouty arthritis, osteoarthritis, systemic lupus erythematosus and juvenile arthritis. Form B would be useful in the treatment of asthma, bronchitis, menstrual cramps, preterm labor, tendinitis, bursitis, liver disease including hepatitis, skin-related conditions such as psoriasis, eczema, burns and dermatitis, and from post-operative inflammation including from ophthalmic surgery such as cataract surgery and refractive surgery. Form B also would be useful to treat gastrointestinal conditions such as inflammatory bowel disease, Crohn's disease, gastritis, irritable bowel syndrome and ulcerative colitis. Form B would be useful for the prevention or treatment of cancer, such as colorectal cancer, and cancer of the breast, lung, prostate, bladder, cervix and skin. Form B would be useful in treating glaucoma, angiogenesis and retinopathies. Form B would be useful in treating inflammation in such diseases as vascular diseases including atherosclerosis, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. Form B would also be useful in the treatment of ophthalmic diseases, such as retinitis, conjunctivitis, retinopathies, uveitis, ocular photophobia, and of acute injury to the eye tissue. Form B would also be useful in the treatment of pulmonary inflammation, such as that associated with viral infections and cystic fibrosis. Form B would also be useful for the treatment of certain central nervous system disorders, such as cortical dementias including Alzheimer's disease, and central nervous system damage resulting from stroke, ischemia, seizures and trauma. Form B is useful as antiinflammatory agents, such as for the treatment of arthritis, with the additional benefit of having significantly less harmful side effects. Form B would also be useful in the treatment of allergic rhinitis, respiratory distress syndrome, endotoxin shock syndrome, osteoporosis and inhibiting bone resorption. Form B also would be useful in the treatment of pain, but not limited to postoperative pain, dental pain, muscular pain, and pain resulting from cancer. Form B would be useful for the prevention of cardiovascular disease, such as atherosclerosis, liver disease and dementias, such as Alzheimer's Disease.

Besides being useful for human treatment, this form is also useful for veterinary treatment of companion animals, exotic animals and farm animals, including mammals, rodents, and the like. More preferred animals include horses, dogs, and cats.

The present Form B may also be used in co-therapies, partially or completely, in place of other conventional antiinflammatories, such as together with steroids, NSAIDs, 5-lipoxygenase inhibitors, $LTB_4$ receptor antagonists and $LTA_4$ hydrolase inhibitors.

Suitable $LTA_4$ hydrolase inhibitors include RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(3-(1E,3E-tetradecadienyl)-2-oxiranyl)benzoic acid lithium salt (Searle).

Suitable $LTB_4$ receptor antagonists include, among others, ebselen, linazolast, ontazolast, Bayer Bay-x-1005, Ciba Geigy compound CGS-25019C, Leo Denmark compound ETH-615, Merck compound MAFP, Terumo compound TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present form also may be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2–1294, ICI-204448, CT-3, CP-99,994, and CP-99,994.

The present invention comprises a pharmaceutical composition comprising a therapeutically-effective amount of crystalline Form B of 4-[5-methyl-3-phenylisoxazol-4-yl]benzenesulfonamide in association with at least one pharmaceutically-acceptable carrier, adjuvant or diluent.

Also embraced within this invention is a class of pharmaceutical compositions comprising crystalline Form B in association with one or more non-toxic, pharmaceutically-acceptable carriers and/or diluents and/or adjuvants (collectively referred to herein as "carrier" materials) and, if desired, other active ingredients. Form B of the present invention may be administered by any suitable route, preferably in the form of a pharmaceutical composition adapted to such a route, and in a dose effective for the treatment intended. The active Form B and compositions may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compound and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of Form B to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

Form B can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0–5 to 20%, advantageously 0.5 to 10% and particularly about 1.5% w/w.

For therapeutic purposes, Form B is ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The crystalline Form B may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

What is claimed is:

1. A crystalline form of 4-[5-methyl-3-phenylisoxazol-4-yl]benzenesulfonamide having a melting point of about 170–174° C.

2. A form of claim 1 having an IR spectrum with the following peaks: 1170, 925, 844, and 729 cm$^{-1}$.

3. A form of claim 1 having an IR spectrum without a significant peak at 723 cm$^{-1}$.

4. A form of claim 1 having an x-ray powder diffraction pattern with the following peaks: 12.221, 15.447, 17.081, 19.798 and 23.861.

5. A pharmaceutical composition comprising a therapeutically-effective amount of crystalline Form B of 4-[5-methyl-3-phenylisoxazol-4-yl]benzenesulfonamide in association with at least one pharmaceutically-acceptable carrier, adjuvant or diluent.

6. A method of treating a cyclooxygenase-2 associated disorder in a subject, said method comprising treating the subject having or susceptible to said disorder with a therapeutically-effective amount of the crystalline Form B of 4-[5-methyl-3-phenylisoxazol-4-yl]benzenesulfonamide.

7. The method of claim 6 for use in treatment of inflammation.

8. The method of claim 6 for use in treatment of arthritis.

9. The method of claim 6 for use in treatment of pain.

10. The method of claim 6 for use in treatment of fever.

11. A method of preparing crystals of claim 1 comprising dissolving 4-[5-methyl-3-phenylisoxazol-4-yl]benzenesulfonamide in an alcohol based solvent system form a solution and slowly cooling the solution.

12. The method of claim 11 wherein the solvent system comprises one or more solvents selected from methanol, isopropanol, aqueous methanol and aqueous ethanol.

13. The method of claim 11 wherein the crystals are recrystallized from a mixture of isopropanol and methanol.

* * * * *